Nov. 29, 1949. A. KREBS Plant Pat. 901
DWARF POLYANTHA ROSE PLANT
Filed Dec. 19, 1947
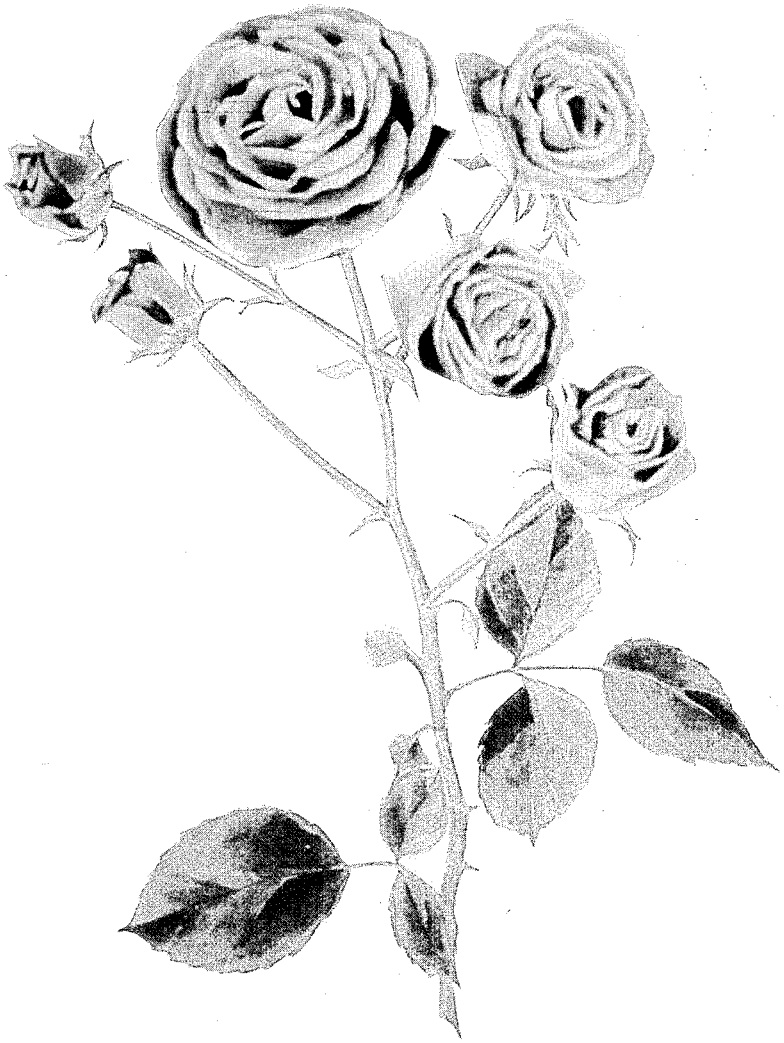
INVENTOR
Alfred Krebs
By Orville M. Kile
Plant Pat. Agt.

Patented Nov. 29, 1949

Plant Pat. 901

UNITED STATES PATENT OFFICE

901

DWARF POLYANTHA ROSE PLANT

Alfred Krebs, Montebello, Calif., assignor to
Howard & Smith, Montebello, Calif.

Application December 19, 1947, Serial No. 792,815

1 Claim. (Cl. 47—61)

My present invention relates to improvements in rose plants of the polyantha type, and resulted from a cross, made by me, of two unnamed seedlings of which one of the earlier progenitors was the Mme. Cecile Brunner. It produces a flower of rich crimson color in rosette form.

The form of this new variety is dwarf and compact and it is heavily foliaged right to the base, making it excellent for use as a pot plant especially since tests under glass have demonstrated it to be a good forcing variety. It is also excellent for corsage work.

This new variety has been asexually reproduced from cuttings, at the greenhouses of Howard & Smith in Montebello, California, and its characteristics appear to be permanent.

Accompanying illustrations show a cluster or truss of buds and blooms in approximately their true colors.

Following is a detailed description of this new rose variety. Color nomenclature refers to the ordinary dictionary meaning of the term, except where plate references are given.

*The plant*

Growth habit and form: Dwarf and compact. Well-branched. Average height about 18 inches. Heavily foliaged right to base of plant for entire season.

Blooming habit: Remontant throughout the season when grown in the open, and throughout the year when grown at 60 degrees under glass. Compact mass of flowers and foliage apparent for full season.

Stems:

*Color.*—Light green.
*Strength.*—Very strong.
*Rigidity.*—Stiff and rigid, with no weak neck. Stems hold trusses in erect position.
*Surface.*—Smooth except for thorns.
*Thorns.*—Numerous, small, brown, alternate on stem, downward-pointing.

Foliage:

*Leaflets.*—3 to 5.
*Quantity.*—Heavily foliaged right to base of plant. When grown in pots, the foliage practically covers the pot.
*Shape.*—Leaflets broadly oval with rounded base and acuminate apex. Edge serrulate.
*Size.*—Terminal leaflet approximately 1¾ to 2 inches long and 1¼ inches wide, with smaller lateral leaflets. Entire leaf 2½ to 3 inches long.
*Texture.*—Leathery.
*Color.*—Dark green.
*Leaf stem.*—Short, slender, light green.
*Stipules.*—Negative.

Bud:

*Size.*—Small, averaging ½ inch long.
*Shape.*—Short, pointed at first, opening into loose rosette form.
*Color.*—Popularly called deep crimson, it would lie between Tyrian Rose and Pomegranate Purple (Plate XII, Ridgway's Color Standards and Nomenclature).
*Opening.*—Slow.
*Peduncle.*—Short, rigid, light green, usually 2 to 3 inches long.
*Calyx and sepals.*—Short but branched; smooth-edged; reflex early.

Bloom:

*Borne.*—In clusters, on many-branched stem.
*Size.*—1 to 1½ inches in diameter.
*Form.*—Close rosette, opening into camellia-like form. In fully open flower, the petals reflex slightly at edge.
*Color.*—Approximately same as bud.
*Discoloration.*—None.
*Petalage.*—Average 30 petals.
*Fragrance.*—Slight.
*Longevity.*—Excellent as cut flower or on plant. Flowers last a week to ten days.

Petals:

*Shape.*—Almost circular but with definite point at tip.
*Aspect.*—Silky. Free from burning in full sun.
*Size.*—About ¾ inch in diameter.
*Color.*—Uniformly deep crimson.
*Arrangement.*—Imbricated. Compact and evenly placed in rosette form as in a camellia.
*Texture.*—Firm and substantial.
*Persistence.*—Petals remain in position until truss passes maturity and then drop cleanly.

Reproductive organs:

*Pistils.*—Dull white.
*Stamens.*—Invisible in open rose. Filaments white and short. Anthers bright yellow. Pollen yellow.
*Fruit.*—None.

Having thus disclosed my invention, I claim:

The new and distinct variety of polyantha rose plant substantially as described and illustrated, characterized particularly by its dwarf, compact and well-branched growth; its heavy foliage to base of plant; its abundantly remontant blooming habit; and its flowers of deep rich crimson having a distinctive rosette form opening camellia-like when fully developed, which flowers last a very long time either on the bush or when cut.

ALFRED KREBS.

No references cited.